United States Patent
Wallace et al.

(10) Patent No.: US 6,355,047 B1
(45) Date of Patent: Mar. 12, 2002

(54) TRACTION FORCE SENSING VACUUM EXTRACTOR

(75) Inventors: William Dean Wallace; Richard A. Dixon; Steven R. Smith; Christopher A. Cutler, all of Murray, UT (US)

(73) Assignee: Clinical Innovations, Murray, UT (US)

( * ) Notice: Subject to any disclaimer, the term of this patent is extended or adjusted under 35 U.S.C. 154(b) by 0 days.

(21) Appl. No.: 09/365,658

(22) Filed: Aug. 2, 1999

Related U.S. Application Data (63) Continuation-in-part of application No. 09/203,003, filed on Nov. 30, 1998, now Pat. No. 6,059,795, which is a continuation-in-part of application No. 09/075,448, filed on May 8, 1998, now Pat. No. 6,074,399.

(51) Int. Cl.$^7$ ............................................... A61B 17/42

(52) U.S. Cl. ........................................ 606/123; 606/122

(58) Field of Search ................................ 606/122, 123, 606/124, 119; 604/73

(56) References Cited

U.S. PATENT DOCUMENTS

| | | | |
|---|---|---|---|
| 2,194,989 A | 3/1940 | Torpin | 128/361 |
| 2,702,038 A | 2/1955 | Uddenberg et al. | 128/361 |
| 2,917,050 A | 12/1959 | Kenyon | 128/361 |
| 3,202,152 A | 8/1965 | Wood et al. | 128/361 |
| 3,207,160 A | 9/1965 | Heyns | 128/361 |
| 3,612,722 A | 10/1971 | Neward | 417/63 |
| 3,765,408 A | 10/1973 | Kawai | 128/352 |
| 3,782,385 A | 1/1974 | Loyd | 128/281 |
| 3,785,381 A * | 1/1974 | Lower | 606/122 |
| 3,794,044 A | 2/1974 | Vennavd et al. | 128/352 |
| 5,019,086 A | 5/1991 | Neward | 606/123 |
| 5,071,403 A | 12/1991 | Larsson | 604/74 |
| 5,224,947 A | 7/1993 | Cooper et al. | 606/123 |
| 5,281,229 A | 1/1994 | Neward | 606/123 |
| 5,395,379 A * | 3/1995 | Deutchman et al. | 606/123 |
| 5,578,043 A * | 11/1996 | Galstian | 606/119 |
| 5,693,058 A | 12/1997 | Cavanagh et al. | 606/123 |
| 5,713,909 A | 2/1998 | Lindsay | 606/123 |
| 5,803,926 A | 9/1998 | Neward | 606/122 |
| 5,810,840 A | 9/1998 | Lindsay | 606/123 |
| 5,849,017 A * | 12/1998 | Reynolds et al. | 606/122 |
| 5,935,136 A | 8/1999 | Hulse et al. | 606/123 |

FOREIGN PATENT DOCUMENTS

| | | |
|---|---|---|
| DE | 1123432 | 2/1962 |
| DE | 3138-589 | 7/1975 |
| SE | A 61 B 17/42 | 3/1955 |
| WO | WO 89/06112 | 7/1989 |

OTHER PUBLICATIONS

Chapter 9, Vacuum Delivery, Operative Obstretrics, pp. 173–189.

CMI Obstetrical Delivery Kit product information, 08/95, Redmond, Oregon, 34 pages.

A Comparison of Different methods of Instrumental Delivery Based on Electronic Measurements of Compression and Traction, Arvind S. Moolgaoker, M.D., Syed O.S. Ahamed, and Peter R. Payne, Feb. 19, 1979, pp. 1–4.

(List continued on next page.)

Primary Examiner—Kevin Truong
(74) Attorney, Agent, or Firm—TraksBritt (57) ABSTRACT

A vacuum extractor for use in childbirth is described. The vacuum extractor includes a handle and a vacuum cup with a force sensor coupled to the vacuum extractor. The force sensor measures the traction force applied between the vacuum cup and the handle for assisting the birthing attendant in applying an appropriate traction force. The force sensor may also include a slipping mechanism which causes the length of the force sensor to distinctly increase if the applied traction force exceeds a certain level such as twenty pounds. Thus, the birthing attendant may feel the slipping and thus determine that the traction force has exceeded the certain value.

14 Claims, 5 Drawing Sheets

OTHER PUBLICATIONS

Handbook of Vacuum Extraction in Obstetric Practice, Aldo Vacca, Edward Arnold, a division of Hodder & Stoghton, 1992, pp 1–27.

Handbook of Vacuum Extraction in Obstetric Practice, Aldo Vacca, 1992, pp 55–62.

The Venthouse; The Obstetric Vacuum Extractor, J.A. Chalmers,, London 1971, 13 pages.

Anwending des Extraktors in der Geburtshilfe; Von V. Finderle, Apr. 1952, pp 16 and 226–230.

Arvind S. Moolgaoker, MD, Syed O.S. Ahamed, and Peter R. Payne, A Comparison of Different Methods of Instrumental Delivery Based on Electronic Measurements of Compression and Traction, Feb. 19, 1979, pp. 1–4.

* cited by examiner

TRACTION FORCE SENSING VACUUM EXTRACTOR

RELATED APPLICATIONS

This application is a continuation-in-part of U.S. patent application Ser. No. 09/203,003, filed Nov. 30, 1998, now U.S. Pat. No. 6,059,795 which is incorporated herein by reference in its entirety. That application is a continuation-in-part of U.S. patent application Ser. No. 09/075,448, filed May 8, 1998 now U.S. Pat. No. 6,074,399.

BACKGROUND OF THE INVENTION

1. The Field of the Invention

The present invention relates to obstetrical instruments and methods. Specifically, the present invention relates to a vacuum extractor that regulates traction force.

2. The Prior State of the Art

One need not be a parent to realize the importance of improved medical devices and methods in delivering a fetus safely into this world. Currently, there are two major methods for delivering a fetus, the Cesarean section delivery and the vaginal delivery.

In Cesarean section deliveries, the fetus is delivered through an incision made in the uterus and a corresponding incision made in the abdomen. An upward-pulling force is required in order to pull the fetus through the incisions and out of the mother. Often, the force is provided by the childbirth attendant's hands directly pulling the fetus through the abdominal incision.

In vaginal deliveries, the fetus is delivered through the vaginal passage after the cervix has fully dilated and effaced. Passing the fetus through the vaginal passage requires that the vaginal muscles be forced to stretch because the fetal head is much larger than the vaginal passage under normal circumstances.

Some stretching force is applied to the vaginal tissues by the mother herself. The involuntary contractions of the uterus during labor push the fetus (typically the fetal head) into the vaginal passage to stretch the vaginal tissues. The stretching force of these involuntary uterine contractions is combined with the stretching force caused by voluntary contractions of the mother's abdominal muscles as the mother tries to push the fetus out of the uterus.

Often, the forces described above are not strong enough or are not medically advisable to use in extracting the fetus. Supplementary force may be applied with a fetal vacuum extractor, for example, in conditions of dystocia (i.e., slow or difficult labor or delivery), uterine inertia, maternal exhaustion, maternal distress, or fetal distress.

In a conventional fetal vacuum extractor, a vacuum cup is sealed over a portion of the fetal head (e.g., the occiput). A flexible tube connects the vacuum cup to a vacuum pump operated by a secondary operator such as a nurse. The vacuum pump allows the nurse to provide a vacuum within the vacuum cup, thereby creating suction between the fetal head and the vacuum cup. As long as a sufficient vacuum is maintained, the primary operator, such as a physician, may pull on the vacuum cup handle, thereby applying traction (i.e., a pulling, delivering force) to the fetal head.

The convention fetal vacuum extractor is useful in providing traction to the fetal head. However, the magnitude of the traction force needs to be controlled for the duration of the contraction. If the traction force is too weak, the force will be insufficient to significantly assist in childbirth. However, if the traction force is too strong, the fetus or the mother may be subject to a higher risk of injury.

Historically, traction forces as high as fifty pounds have been used to extract the fetus. However, recently, there have been reports of fetal compromise such as subgaleal hematomas causes by excessive traction force. Specifically, excessive traction forces can dislodge the scalp from its periosteal surface breaking capillaries and blood vessels.

Proper use of the vacuum extractor is dependent principally upon the proper application of the vacuum cup to the fetal head. When the vacuum cup is placed upon the flexion point (three centimeters forward of the posterior fontanelle along the sagittal suture) of the fetal head, the least diameter of the fetal head is presented through the birth canal. This causes less resistance and, therefore, lower traction forces are required to assist in fetal vaginal deliveries where vacuum cups are used.

Typically, a traction force of approximately twenty pounds is all that is needed to assist in vaginal deliveries if the vacuum cup is properly applied. However, more or less traction force may also be appropriate as determined by a licensed, medically competent childbirth attendant. The major determinant is that progress of the fetal head descent is made with each contraction.

Currently, childbirth attendants typically estimate the amount of traction force being applied by sense of touch. In other words, the childbirth attendant by experience determines whether the amount of traction force is too great, too small, or acceptable. While childbirth attendants, and particularly physicians, are typically competent to judge what is an acceptable amount of traction force, even physicians may often misjudge the amount of traction force being applied. In the case of a misjudgement, the traction may be insufficient to assist in childbirth, or the traction may be great enough to cause injury to the fetus or mother.

Therefore, what is desired is a system and method for providing information regarding traction force while the childbirth attendant is using a vacuum extractor for use in childbirth.

SUMMARY OF THE INVENTION

The present invention includes a vacuum extractor for use in childbirth. The primary function of this vacuum extractor is to apply traction force to the fetus (typically the fetal head) when the natural force provided by the mother is insufficient or inadvisable to use in completing childbirth. A childbirth attendant will typically be educated as to the amount of traction force that may be safely and effectively applied to the fetus. Typically, the childbirth attendant will judge the amount of traction force by sensing how much force he or she feels is being applied.

The present invention provides a mechanism where a childbirth attendant can objectively know the amount of traction force being applied. Specifically, a force sensor is coupled to the vacuum cup. The force sensor indicates the amount of traction force to the childbirth attendant. The force sensor may include a gauge that allows the childbirth attendant to visually determine the amount of force being applied. For example, a spring in the mechanism may compress in response to traction force, causing the position of a marker connected to the spring to change. The traction force may thus be determined by comparing the position of the marker with a scale provided on the force sensor.

The force sensor may also include a slipping mechanism whereby the childbirth attendant feels when a predetermined level of traction force has been exceeded. Specifically, when the predetermined level of traction force is exceeded, the length of the force sensor suddenly increases or slips, for example, approximately one inch. This slipping can be easily felt by the childbirth attendant. At this point, the childbirth attendant may choose to continue traction. Alternatively, the childbirth attendant may discontinue traction, causing a restoration mechanism to return the vacuum extractor to its unslipped position.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention relates to a vacuum extractor and method for use in childbirth. Unlike conventional vacuum extractors, the vacuum extractor of the present invention senses the amount of traction force applied. The vacuum extractor may also include a mechanism for indicating when the amount of traction force exceeds a certain level. For example, if the traction force exceeds twenty pounds, the handle may slip slightly away from the vacuum cup, indicating to the childbirth attendant that the traction force has exceeded twenty pounds.

While the vacuum extractor of the present invention is described with respect to the following specific embodiments, these embodiments are illustrative only and not limiting. Throughout this description, like symbols in different figures indicate the same or similar elements.

Figure 1:
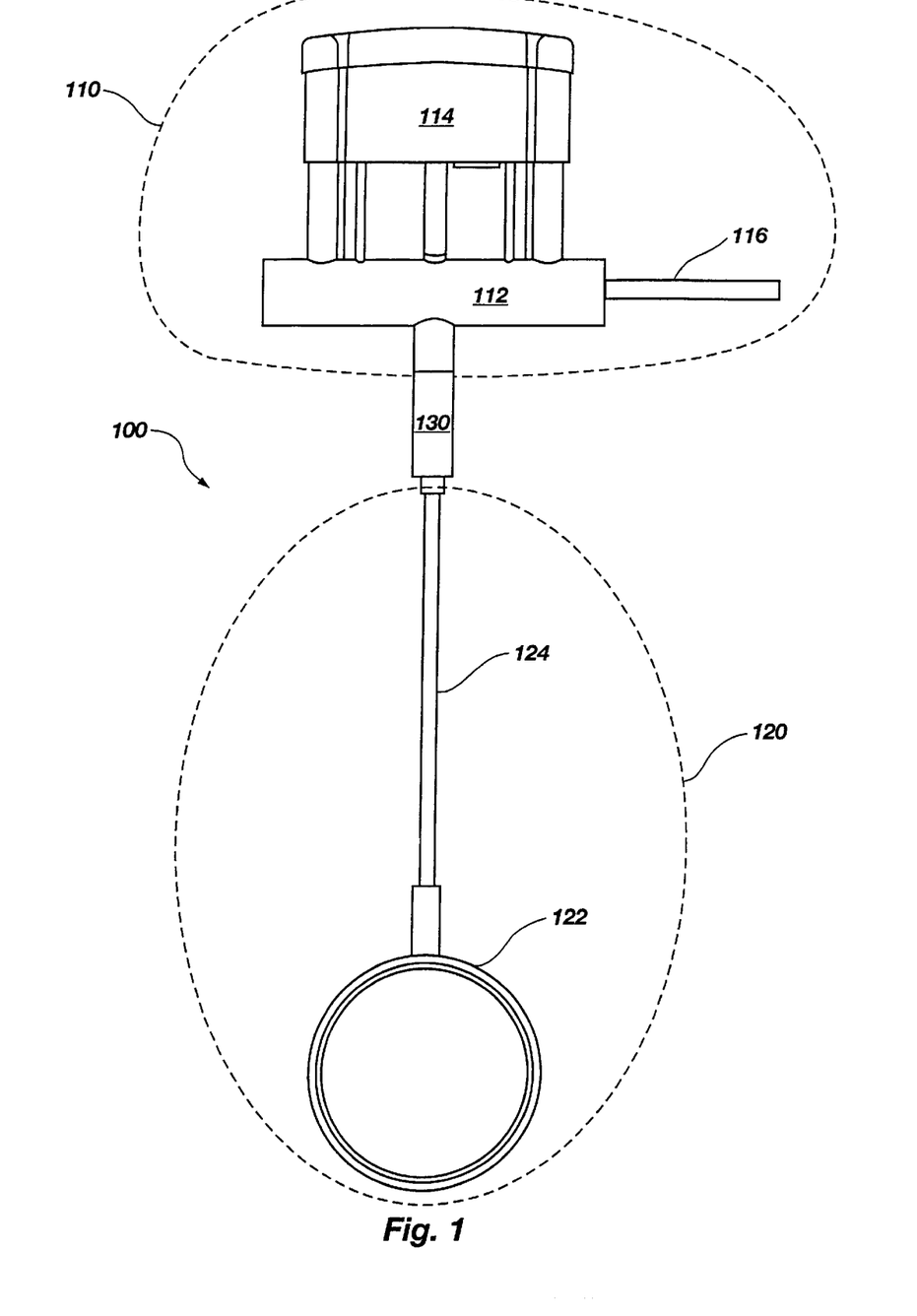
FIG. 1 is a diagram of a traction force-regulating vacuum extractor according to one embodiment of the present invention.

FIG. 1 illustrates a vacuum extractor 100 having three general components: a handle 110, a vacuum cup 120 coupled to the handle 110, and a force sensor 130 coupling the handle 110 and vacuum cup 120 together. The force sensor 130 measures the traction force applied to the vacuum extractor 100. In this description and in the claims, "coupled" is defined as being either directly connected, as when two objects contact each other, or indirectly connected through intermediary mediums. Thus, two objects which may never contact each other may still be "coupled" for the purposes of this description and the accompanying claims.

The designs of the handle 110 and the vacuum cup 120 are not critical to the present invention. Any vacuum extractor handle and vacuum cup for use in childbirth may be used in the present invention. All that is required is that the handle 110 be used to apply traction force, and that the vacuum cup 120 be used to attach to a fetus during childbirth. Though the present invention is not limited to a particular type of handle or vacuum cup, a specific unconventional design of the handle and vacuum cup is described with reference to FIG. 1.

The handle 110 includes a grip 112, a pump (or "palm chamber") 114, and a vacuum gauge 116. During operation, the childbirth attendant compresses the palm chamber 114 towards the grip 112 and then releases. So long as the force sensor 130 allows fluid to pass from the vacuum cup 120 to the handle 110, this action causes fluid to be drawn from a cup portion 122 of the vacuum cup 120, through the tube 124, and into the handle 110. During operation, the cup portion 122 of the vacuum cup 120 is attached to a fetus; thus a vacuum is drawn in the vacuum cup 120. Once a sufficient vacuum is obtained, as measured by the vacuum gauge 116, the childbirth attendant applies traction force to the fetus by pulling on the grip 112. Although the present invention is not limited to a particular design of the handle 110 or vacuum cup 120, a handle and vacuum cup that can be used in the present invention are described in co-pending U.S. patent application Ser. No. 09/203,003, filed Nov. 30, 1998, which is incorporated herein by reference in its entirety.

Figure 2:
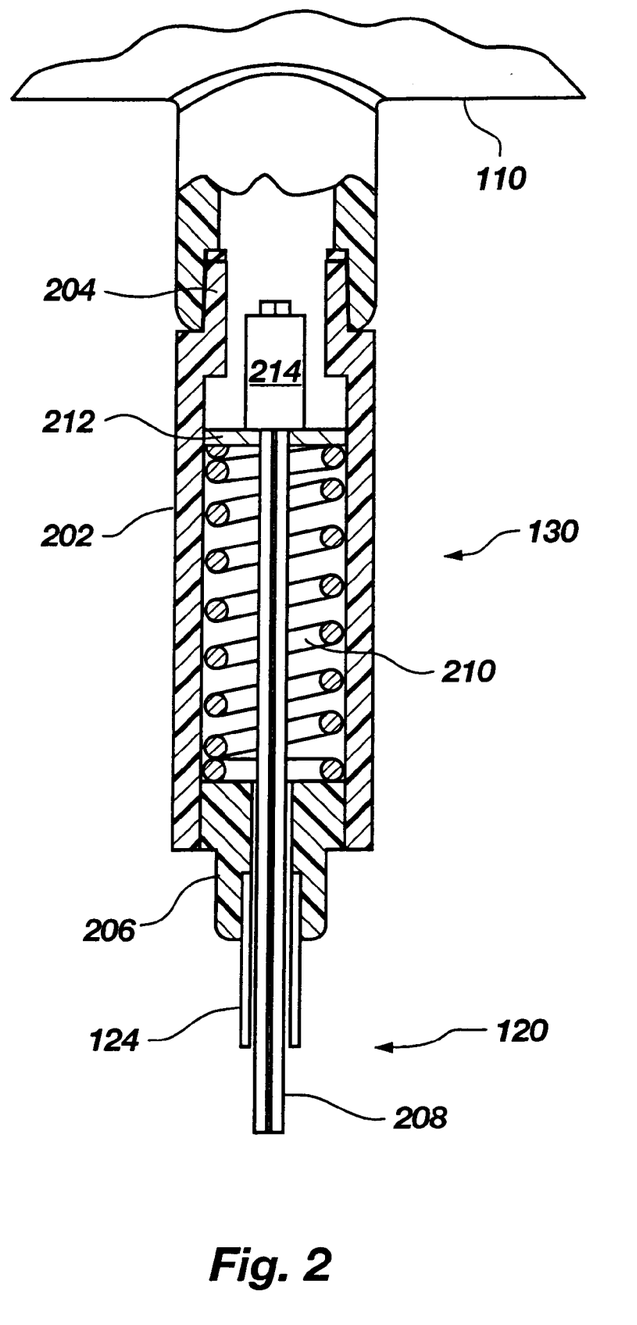
FIG. 2 is a cross-sectional diagram of a first embodiment of the force sensor of FIG. 1.

FIG. 2 is a cross-sectional diagram of one embodiment of the force sensor 130 of FIG. 1. For clarity, portions of the handle 110 and the vacuum cup 120 are also shown to illustrate the interconnection with the handle 110 and the vacuum cup 120. The force sensor 130 operates to measure the traction force applied between the handle 110 and the vacuum cup 120 as will now be described with respect to FIG. 2.

The force sensor 130 includes a cylindrically shaped shell 202 composed of, for example, transparent molded polycarbonate. The shell 202 has an upper insert 204 that compression fits within the handle 110 to provide a substantially tight seal between the upper insert 204 and the handle 110. The inner surface of the shell 202 defines a channel in which a compressible device 210 may reside. The compressible device 210 may be, for example, a coil spring, a dense elastic, or any other calibratable compressible medium. The compressible device 210 may have a constant spring coefficient of, for example, approximately 50 pounds per inch or approximately 100 pounds per inch. However, the spring constant may vary as desired.

A tube connector 206 composed of, for example, molded polycarbonate supports the bottom of the compressible device 210. In this description and in the claims, "bottom" and "downward" mean towards the cup portion 122, and "top" and "upward" mean towards the handle 110. The tube connector 206 is shaped to fit into the bottom of the shell 202 so as to create a substantially tight seal between the tube connector 206 and the shell 202. The tube connector 206 is also shaped to receive the tube 124 of the vacuum cup 120 so as to create a substantially tight seal between the tube connector 206 and the tube 124. Thus, fluid may be drawn upwards from the tube 124 through the shell 202 and into the handle 110. If necessary, a solvent bond or adhesive may be used between the upper insert 204 and the handle 110, between the tube connector 206 and the shell 202, and/or between the tube connector 206 and the tube 124.

A cable 208, which is attached to the cup portion 122 of the vacuum cup 120, extends upward through the tube 124 of the vacuum cup 120, through the tube connector 206, through the compressible device 210, and through the center of a washer 212 situated on top of the compressible device 210. The top of the cable 208 is held by a crimp 214 which keeps the cable 208 from slipping down through the compressible device 210. The cable 208 may be, for example, composed of stainless steel and may include a single strand of cable of approximately 28 mils in diameter doubled on itself and crimped to the cut end of the cable 208. The crimp 214 may be composed of, for example, brass.

When traction force is applied, the tube 124 of the vacuum cup 120 tends to stretch. Since the cable 208 is connected to the cup portion 122 of the vacuum cup 120, this stretching draws the cable 208 downward, causing the crimp 214 to compress the compressible device 210 via the washer 212. Thus, the position of the washer 212 is a function of the applied traction force.

The washer 212 may act as a marker by which a childbirth attendant can judge the amount of traction force by visual inspection of the position of the washer 212. In this case, the shell 202 is composed of a translucent or transparent material so that the washer 212 may be visible to the childbirth attendant. The washer 212 may have a bright color to further increase the visibility of the washer 212. The shell 202 may also have a calibrated label (not shown) adhered or printed on its exterior. The childbirth attendant can then quantify the traction force by comparing the position of the washer 212 with respect to the markers on the calibrated label. In addition, forces greater than twenty pounds may be indicated by a red zone on the calibrated label.

Figure 3A:
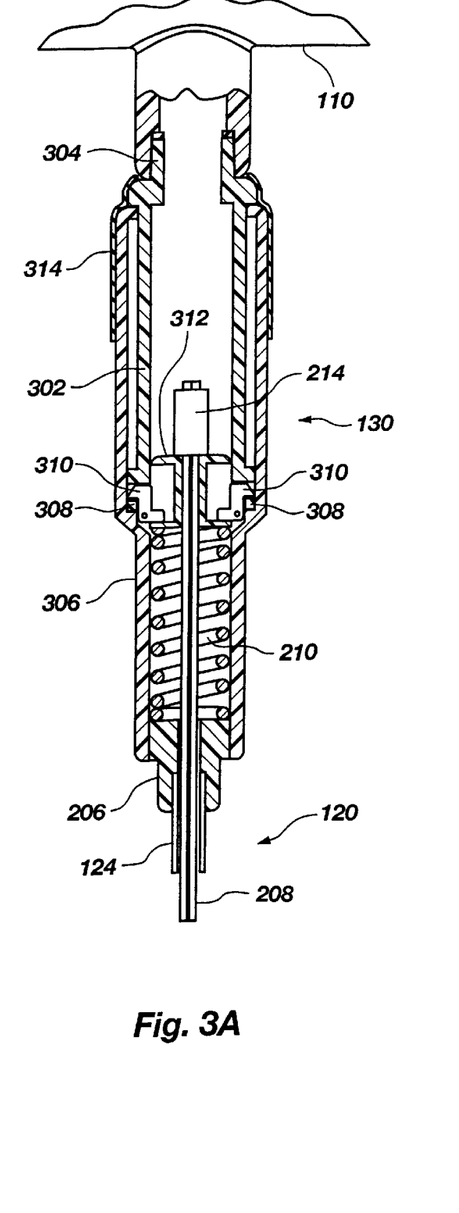
FIG. 3A is a cross-sectional diagram of a second embodiment of the force sensor of FIG. 1 in an unslipped condition.
Figure 3B:
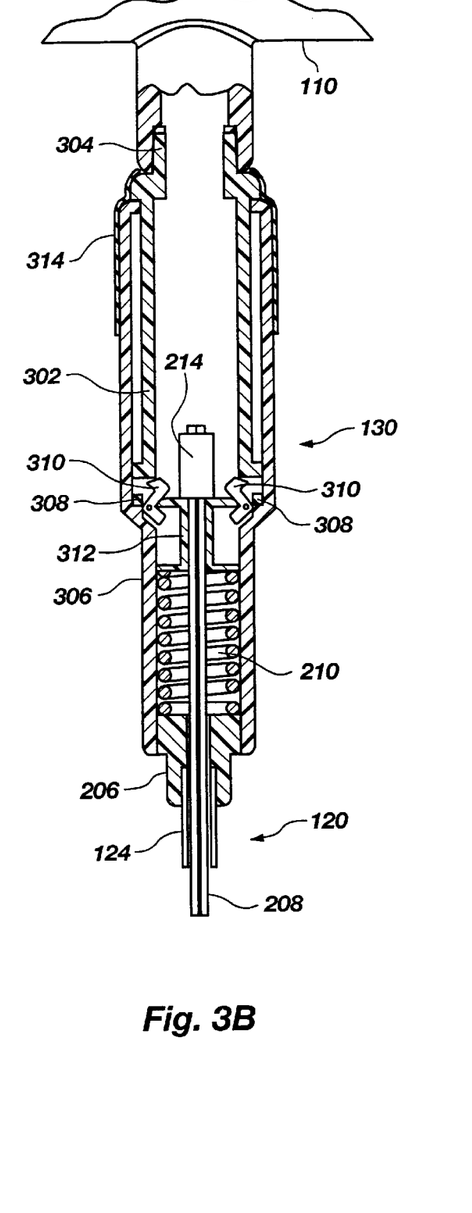
FIG. 3B is a cross-sectional diagram of the force sensor of FIG. 3A as it is about to slip to its slipped condition.
Figure 3C:
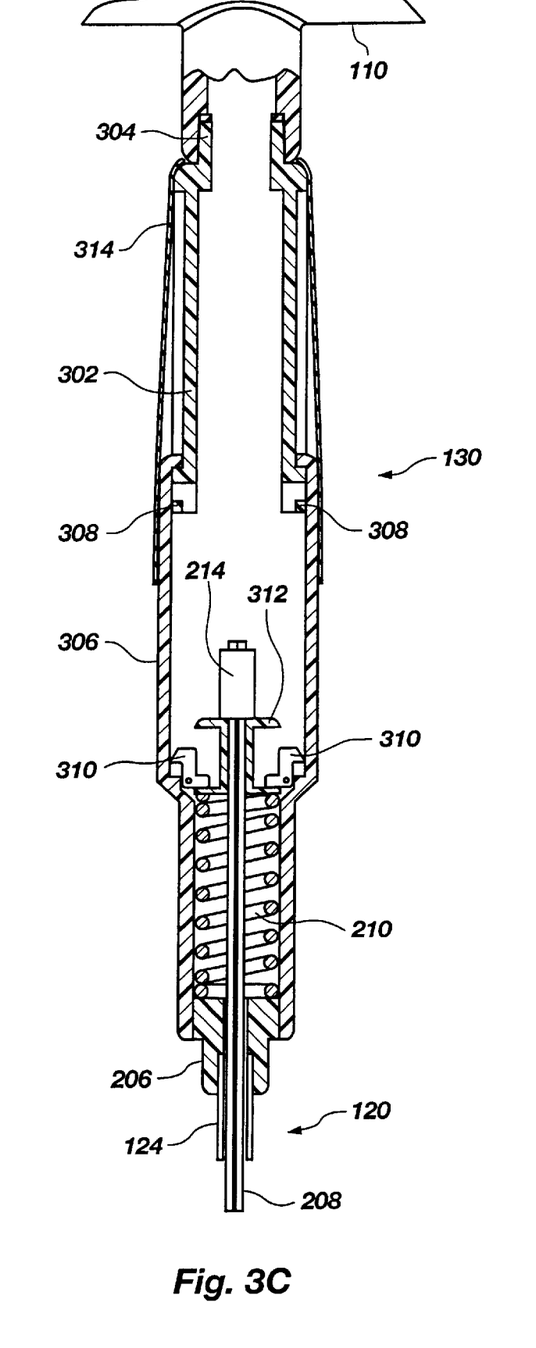
FIG. 3C is a cross-sectional diagram of the force sensor of FIG. 3A in its slipped condition.

FIG. 3A is a cross-sectional diagram of another embodiment of the force sensor 130 of FIG. 1. In this embodiment, the force sensor 130 measures the traction force up to a predetermined level such as, twenty pounds. FIG. 3A shows the force sensor 130 with no applied traction force. FIG. 3B shows the force sensor 130 at the predetermined level such as twenty pounds. Note the compression of the compressible device 210 in FIG. 3B due to the traction force. Once the traction force exceeds the predetermined level, the force sensor 130 suddenly lengthens an appreciable amount such as one inch, causing the handle 110 to suddenly slip the appreciable distance away from the vacuum cup 120. FIG. 3C shows the force sensor 130 in its slipped state. In operation, this slipping is noticed by the childbirth attendant and may be an indication that a safe level of traction force has been exceeded. Even so, the childbirth attendant can choose to either continue applying traction force with the force sensor 130 in its slipped state of FIG. 3C, or return the force mechanism to the unslipped state of FIG. 3A by momentarily ceasing the application of traction force.

Referring to FIGS. 3A, 3B and 3C, the force sensor 130 includes a shell 302 composed of, for example, transparent molded polycarbonate. The shell 302 has an upper insert 304 that compression fits within the handle 110 to provide a substantially tight seal between the upper insert 304 and the handle 110.

A slider shell 306 composed of, for example, transparent molded polycarbonate, is slidably coupled to the shell 302 so that the slider shell 306 is free to slide upwards and downwards over the shell 302 unless the slider shell 306 is locked with respect to the shell 302. An elastic cover 314 provides a restoring force that pulls the slider shell 306 upward absent a traction force.

Normally, the slider shell 306 is locked to the shell 302 as is now described. The shell 302 includes a notch 308. As seen in FIG. 3A, a latch 310 pivotably connected to the slider shell 306 typically grasps hold of the notch 308, thereby preventing vertical movement of the slider shell 306 with respect to the shell 302. In the description and in the claims, this condition is referred to as the "unslipped condition" of the force sensor 130.

The inner surface of the slider shell 306 defines a channel in which the compressible device 210 resides. The tube connector 206 connects the slider shell 306 to the tube 124 in a similar manner as the tube connector 206 connects the shell 202 and the tube 124 in the embodiment of FIG. 2 so that fluid may be drawn from the tube 124, through the slider shell 306, through the shell 302 and into the handle 110.

The cable 208 extends up through the tube connector 206, through the compressible device 210, and through the center of a triggering device 312 situated on top of the compressible device 210. The crimp 214 keeps the cable 208 from slipping down through the compressible device 210.

The operation of the force sensor 130 of FIGS. 3A, 3B and 3C is now described. When no traction force is applied, the force sensor 130 is in the unslipped condition shown in FIG. 3A with the compression device 210 uncompressed. As traction force is applied, the tube 124 of the vacuum cup 120 tends to stretch, causing the cable 208 to pull the triggering device 312 downward, thereby compressing the compressible device 210. A portion of the triggering device 312 may be brightly colored so as to be readily comparable against calibrated labeling on the slider shell 306 to determined traction force.

If the traction force approaches a predetermined level such as twenty pounds, an upper portion of the triggering device 312 causes the latch 310 to rotate away from the notch 308, thus releasing the latch 310 from the notch 308 as shown in FIG. 3B. At this point, the traction force slides the slider shell 306 away from the handle 10 an appreciable distance such as one inch until the slider shell 306 is mechanically stopped as shown in FIG. 3C. In this description and in the claims, this condition is referred to as a "slipped condition."

Once the force sensor 130 has slipped, the childbirth attendant has several options. The childbirth attendant may choose to continue applying traction in this slipped condition. If so, the force sensor continues to measure traction force in the same manner as in the unslipped condition. The only difference is that the force sensor 130 is lengthened.

The childbirth attendant may also choose to reset the force sensor 130 back into the unslipped condition. This may be accomplished by discontinuing traction so that the elastic cover 314 pulls the slider shell 306 back up until the latch 310 is once again engaged with the notch 308 as shown in FIG. 3A.

Using the embodiment of the force sensor 130 of FIGS. 3A, 3B and 3C, the childbirth attendant may monitor the traction force as well as receive a distinct signal when a predetermined important level of traction force is applied.

Figure 4:
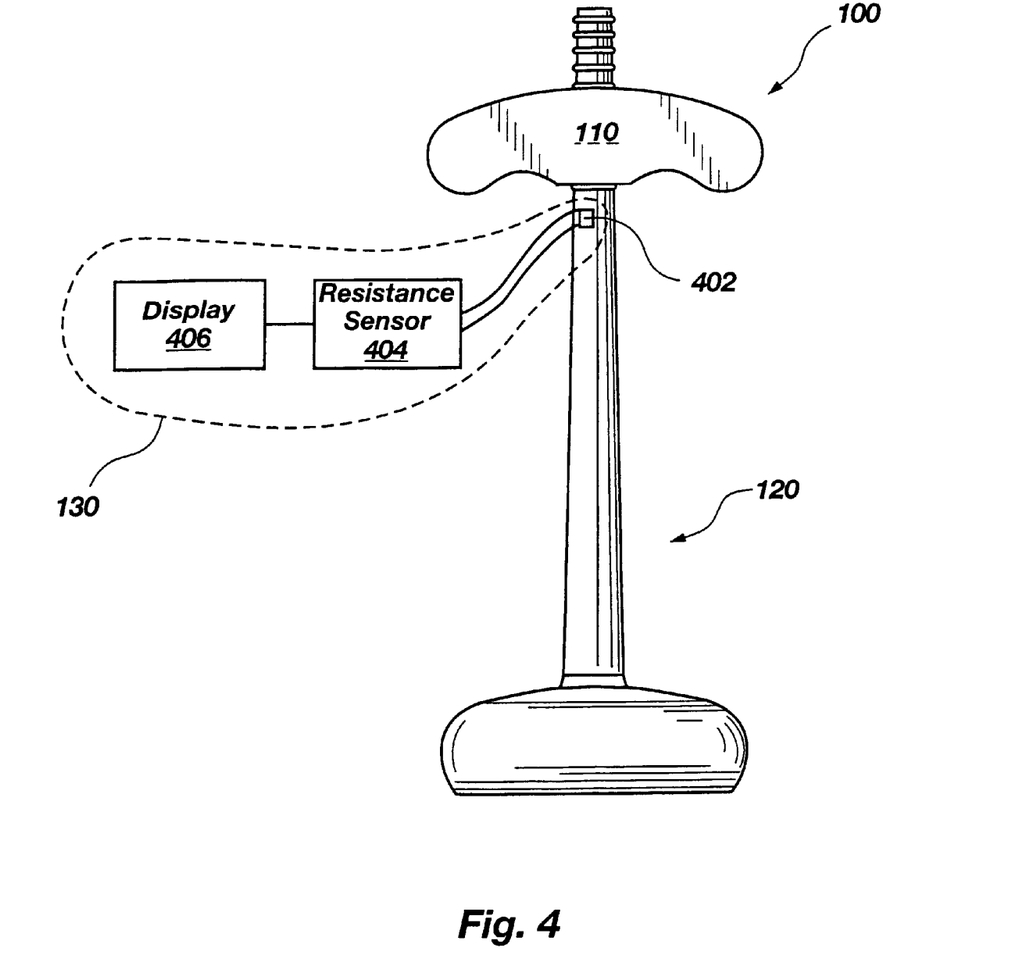
FIG. 4 is a diagram of a traction force-regulating vacuum extractor according to a second embodiment of the invention.

FIG. 4 shows yet another embodiment of the vacuum extractor 100 also including a handle 110 and a vacuum cup 120. Here, the force sensor 130 includes a commonly available electronic semiconductor force sensor gauge 402 that is affixed to the vacuum cup 120 near the handle 110. The force sensor gauge 402 has a resistive element that changes resistance with even very slight strain. Thus, if the two sides of the resistive element are affixed to the vacuum cup 120, strain in the vacuum cup 120 will cause strain and a corresponding change in resistance in the resistive element of the force sensor gauge 402. This is made possible because the vacuum cup 120 is subject to strain.

A commonly available force resistance sensor 404 may be used to measure the resistance of the force sensor gauge 402. This resistance is a function of the traction force applied. Thus, the traction force can be displayed on the display 406. Thus, the childbirth attendant can determine the traction force by reading the display 406.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A vacuum extractor for use in childbirth comprising:
    a vacuum cup;
    a handle coupled to the vacuum cup; and
    a force sensor coupled to the vacuum cup, wherein the force sensor is configured to measure a traction force applied by the handle to the vacuum cup.

2. The vacuum extractor of claim 1, wherein the force sensor couples the handle to the vacuum cup.

3. The vacuum extractor according to claim 2, wherein the vacuum cup comprises a cup portion and a tube, wherein the vacuum extractor further comprises:
    a cable coupled to the cup portion and extending from the cup portion through the tube and into the force sensor; and
    a compressible device within the force sensor, wherein the cable is coupled to the compressible device such that when a traction force is applied and the vacuum cup stretches, the cable is drawn towards the cup portion, and the compressible device is compressed.

4. The vacuum extractor according to claim 3, wherein the force sensor further comprises:
    a tube connector connected to the tube of the vacuum cup, wherein the tube connector provides a support for the compressible device at one end of the compressible device; and
    a crimp holding the cable from falling back through the compressible device.

5. The vacuum extractor of claim 4, further comprising:
    a washer situated on a side of the compressible device opposite from the tube connector, wherein the crimp is sized so that the crimp can not fit through the washer and wherein the crimp and the washer are configured to keep the cable from falling back through the compressible device.

6. The vacuum extractor of claim 3, wherein the compressible device comprises a coil spring.

7. The vacuum extractor of claim 3, wherein the compressible device comprises a dense elastic.

8. The vacuum extractor of claim 3, wherein the compressible device has a spring constant of approximately 50 pounds per inch or less.

9. The vacuum extractor of claim 3, wherein the compressible device has a spring constant of approximately 100 pounds per inch.

10. The vacuum extractor according to claim 3, wherein the compressible device includes a marker, wherein compression of the compressible device causes a position of the marker to change.

11. A vacuum extractor for use in childbirth comprising:
    a vacuum cup;
    a handle coupled to the vacuum cup; and
    a force sensor coupled between the handle and the vacuum cup, wherein the force sensor comprises a slipping mechanism configured to suddenly increase the length of the force sensor in the direction of traction when a traction force exceeds a predetermined level.

12. The vacuum extractor according to claim 11, wherein the predetermined level is approximately twenty pounds.

13. The vacuum extractor according to claim 11, wherein the vacuum cup comprises a cup portion and a tube, wherein the force sensor comprises:
    a shell rigidly coupled to the handle;
    a slider shell slidably coupled to the shell;
    a cable coupled to the cup portion and extending from the cup portion through the tube and into the force sensor;
    a compressible device within the force sensor;
    a tube connector connected to the tube of the vacuum cup, wherein the tube connector provides a support for the compressible device at one end of the compressible device;
    a triggering device keeping the cable from falling back through the compressible device; and
    a latch configured to rigidly couple the slider shell to the shell when the vacuum cup is in an unslipped condition, wherein movement of the triggering device towards the tube compresses the compressible device and releases the latch so that the vacuum cup slips into a slipped condition.

14. A vacuum extractor for use in childbirth comprising:
    a vacuum cup comprising a cup portion and a tube;
    a handle coupled to the vacuum cup;
    a force sensor coupled to the handle of the vacuum cup, wherein the force sensor is configured to measure the traction force applied by the handle to the vacuum cup;
    a cable coupled to the cup portion and extending from the cup portion through the tube and into the force sensor; and
    a compressible device within the force sensor, wherein the cable is coupled to the compressible device such that when a traction force is applied and the vacuum cup stretches, the cable is drawn towards the cup portion, and the compressible device is compressed.

* * * * *

UNITED STATES PATENT AND TRADEMARK OFFICE
CERTIFICATE OF CORRECTION

PATENT NO. : 6,355,047 B1
DATED : March 12, 2002
INVENTOR(S) : William Dean Wallace et al.

It is certified that error appears in the above-identified patent and that said Letters Patent is hereby corrected as shown below:

Column 6,
Line 42, change "10" to -- 110 --

Signed and Sealed this

Sixteenth Day of March, 2004

JON W. DUDAS
*Acting Director of the United States Patent and Trademark Office*